United States Patent
Shaw et al.

[11] Patent Number: 6,149,432
[45] Date of Patent: Nov. 21, 2000

[54] BUTTRESS THREAD DENTAL IMPLANT

[75] Inventors: Leon Shaw, Delray Beach; Bruce Hollander, Deerfield Beach, both of Fla.

[73] Assignee: Biolok International, Inc., Deerfield Beach, Fla.

[21] Appl. No.: 09/312,114

[22] Filed: Jan. 4, 1999

Related U.S. Application Data

[63] Continuation-in-part of application No. 08/172,702, Dec. 27, 1993, Pat. No. 5,964,766.

[51] Int. Cl.⁷ .................................................. A61C 8/00
[52] U.S. Cl. .................................................. 433/174
[58] Field of Search .................. 433/173, 174, 433/201.1

[56] References Cited

U.S. PATENT DOCUMENTS

| | | | |
|---|---|---|---|
| 4,324,550 | 4/1982 | Reuther et al. | 433/174 |
| 4,468,200 | 8/1984 | Munch | 433/174 |
| 5,007,385 | 4/1991 | Valen | 433/174 |
| 5,199,873 | 4/1993 | Schulte et al. | 433/174 |
| 5,302,126 | 4/1994 | Wimmer et al. | 433/174 |
| 5,312,255 | 5/1994 | Bauer | 433/174 |
| 5,967,783 | 10/1999 | Ura | 433/174 |

*Primary Examiner*—Nicholas D. Lucchesi
*Attorney, Agent, or Firm*—M K Silverman

[57] ABSTRACT

A dental implant includes a rigid body having axially symmetric and radially circumferential spiral pitch surfaces, in a range of about 22 to about 28 pitch surfaces per axial inch, an upper concave bevel surface above each pitch surface, which is longer than a lower bevel surface beneath each pitch surface, and an intersection of each plane of each pitch surface, and each plane of each lower bevel surface defining a total included angle in a range of about 90 to about 130 degrees, the rigid body having minor thread diameters at intersections, between pitch surfaces, of the upper and lower bevel surfaces, the pitch surfaces and the minor thread diameters defining, at any axial radius of the rigid body, a ratio of thread pitch to thread depth in a range of about 1.25:1 to about 1.40:1. Each of the lower bevel surfaces define a total included angle in a range of about 20 to about 30 degrees relative to any given axial radius of the implant at a minor thread diameter.

16 Claims, 3 Drawing Sheets

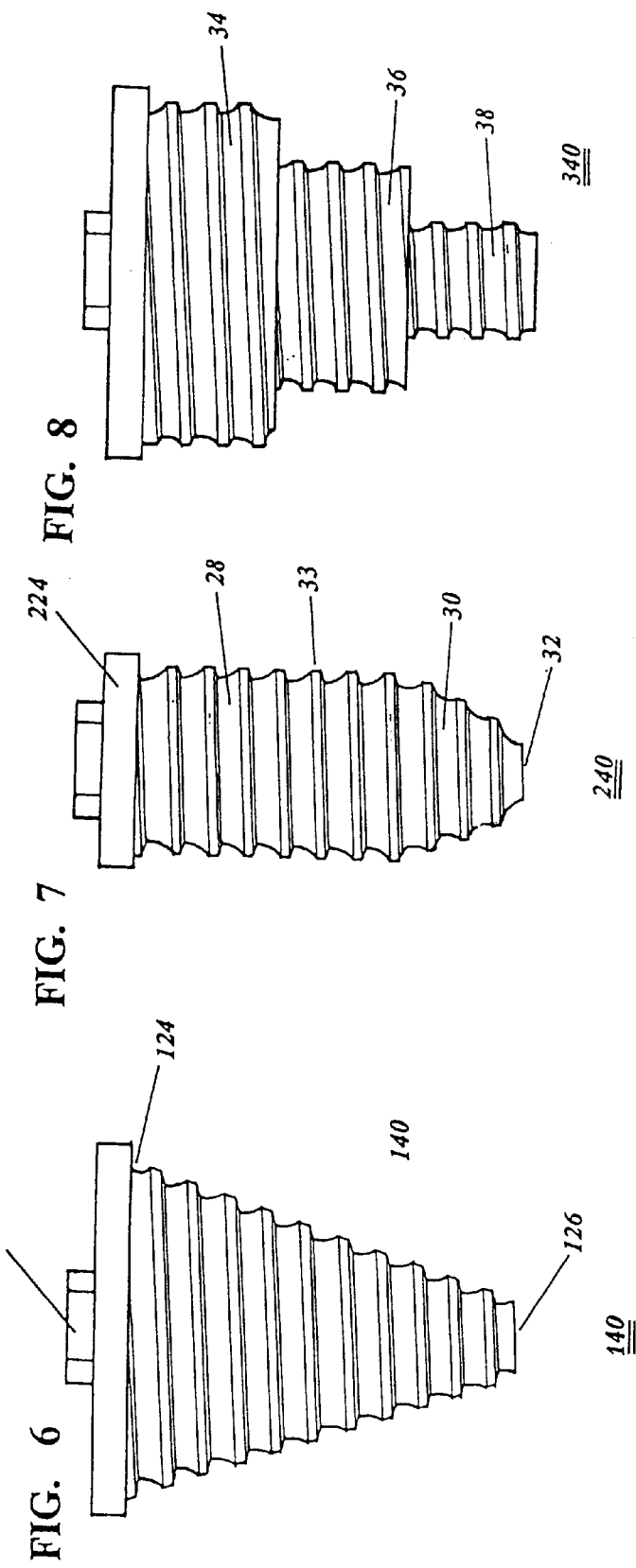

BUTTRESS THREAD DENTAL IMPLANT

REFERENCE TO RELATED APPLICATION

This case is a continuation-in-part of application Ser. No. 08/172,702, filed Dec. 27, 1993, now U.S. Pat. No. 5,964,766, entitled Buttress Thread Dental Implant.

BACKGROUND OF THE INVENTION

The present invention relates to the external configuration of a dental implant element and, more particularly, to a specific beneficial screw-like geometry for use with such an implant.

The prior art of dental implants has generally related to the use of forty pitch threading (0.025 inches between threads) having an essentially symmetric bevel as between the upper and lower faces on either side of the major thread diameters of the threading of such implant elements. In such symmetry, the standard total included angle at the so-called bevel surface at the outer geometry of the major thread diameter has, historically, comprised an angle of about sixty degrees. Therein the distance between threads was generally equal to the thread depths. See FIGS. 1A and 1B.

The within inventor has discovered that a screw-like implant surface of the above type is not optimal from an anatomical perspective. More particularly, the inventor has, as a result of extended experimentation in the subject area, determined that the so-called spongy layer of bone, of which the upper and lower human mandible is formed, does not optimally engage threaded implant surfaces having a forty pitch and greater thread characteristic. The inventor has also discovered that the prior art symmetric bevel is not nearly as effective as would be an asymmetric upper-to-lower face configuration, as is more particularly set forth below.

As a consequence of the above limitations in the prior art, dental implants in the human mandible are prone to movement and loosening over time, particularly as the cumulative effect of the thousands of micro-forces, torques, stresses and strains at the bone implant interface occur. It is in response to these well known shortcomings in the prior art that the instant invention is directed.

SUMMARY OF THE INVENTION

A dental implant includes a rigid body having thereupon axially symmetric and radially circumferential spiral pitch surfaces, in a range of about 22 to about 28 pitch surfaces per axial inch, an upper concave bevel surface above each pitch surface, which is longer than a lower bevel surface beneath each pitch surface, and an intersection of each plane of each pitch surface, and each plane of each lower bevel surface defining a total included angle in a range of about 90 to about 130 degrees, said rigid body having minor thread diameters at intersections, between pitch surfaces, of said upper and lower bevel surfaces, said pitch surfaces and said minor thread diameters defining, at any axial radius of said rigid body, a ratio of thread pitch to thread depth in a range of about 1.25:1 to about 1.40:1. Each of said lower bevel surfaces define a total included angle in a range of about 20 to about 30 degrees relative to any given axial radius of said implant at a minor thread diameter thereof.

It is an object of the present invention to provide a buttress-thread dental implant having superior characteristics of gripping to the mandible bone interface and of resistance to micro-mechanical movements, stresses and the like.

It is another object to provide an improved dental implant having improved characteristics of axial and rotational stability relative to the anatomical bone interface and superior self-tapping ability over the prior art.

It is a further object of the present invention to provide an improved dental implant surface having enhanced durability as compared to such prior art structures.

The above and other objects and advantages of the present invention will become apparent from the hereinafter set forth Brief Description of the Drawings, Detailed Description of the Invention and Claims appended herewith.

BRIEF DESCRIPTION OF THE DRAWINGS

FIG. 6 is an elevational view of a variation of the first embodiment of the instant invention.

FIG. 7 is an elevational view of a second embodiment of the instant invention.

FIG. 8 is an elevational view of a third embodiment of the instant invention.

DETAILED DESCRIPTION OF THE INVENTION

Figure 1B:
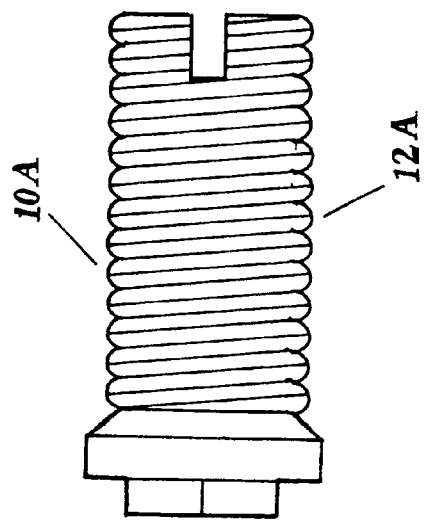
FIGS. 1A and 1B are a cross-sectional views of prior art dental implants showing the threaded surface thereof.
Figure 1A:
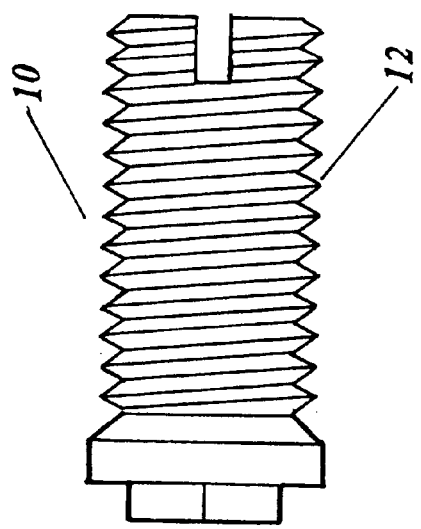

FIGS. 1A and 1B show a typical prior art screw implants 10 and 10a having a plurality of radially symmetric upper and lower bevel surfaces 12 and 12a. As noted in the Background of the Invention above, such prior art implants will typically have forty pitches (threads) or more to an axial inch of screw length.

Figure 5:
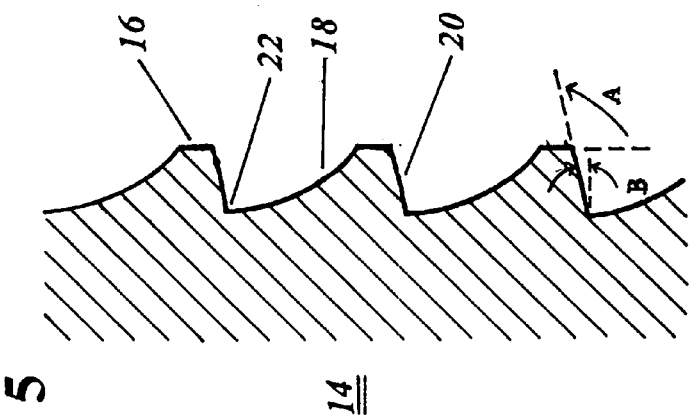
FIG. 5 is an enlarged fragmentary view of the bevel surface geometry of the invention.
Figure 3:
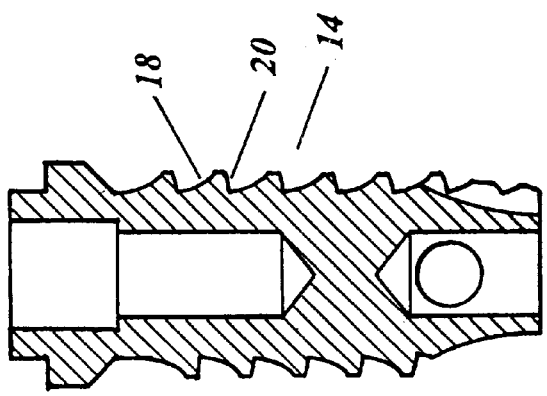
FIG. 3 is an axial cross-sectional view of FIG. 2.
Figure 4:
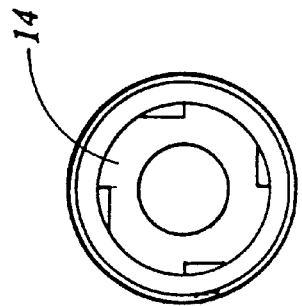
FIG. 4 is a bottom plan view of the implant of FIG. 2.
Figure 2:
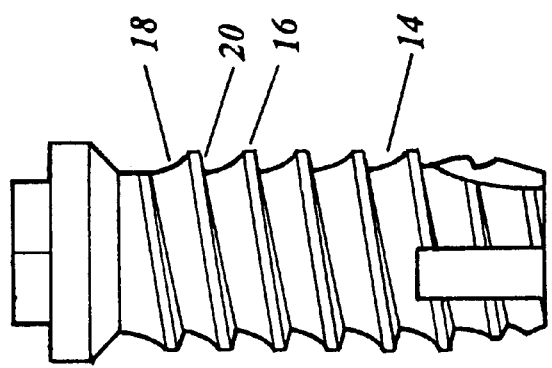
FIG. 2 is an elevational view of the surface of a dental implant in which the rigid body of thereof defines an envelope in the form of a conical section.

A first embodiment of a dental implant 14 is shown in the elevational view of FIG. 2, the cross sectional view of FIG. 3, the bottom view of FIG. 4 and the enlarged bevel surface view of FIG. 5. As may be noted, the envelope of the implant defines a conical segment. The ratio of the major-to-minor bases 24 and 26 respectively may vary from about 1.5:1.0 as much as about 4.0:1.0 (see FIG. 6). Therein, the invention may be seen to comprise a so-called buttress-thread screw-like body having in the range of about twenty-two to about twenty-eight pitch surfaces 16 per inch. A preferred mode of the present invention has been determined to be about twenty-five pitch surfaces per axial inch, that is, 0.040 inches between threads.

The invention is further characterized by a particular relationship in geometry of upper bevel surface 18 to lower bevel surface 20. See particularly FIG. 5. As may be noted, the upper bevel surface is substantially longer (by a ratio of more than two to one) than lower bevel surface 20. Also, said upper surface 18 is concavely curved at a radius of about 0.040 inches, while lower bevel surface 20 is substantially flat. It is noted that in a preferred embodiment the major thread diameter, which corresponds to the location of pitch surface 16 in FIG. 5, is 0.142 inches and the minor thread diameter 22 is about 0.112 inches. Accordingly, the difference between major and minor thread diameters, i.e., the thread depth is about 0.030 inches. Also the ratio of major-to-minor threads diameter is in the range of 1.2:1 to 1.3:1.

A further defining characteristic of the geometry of the instant dental implant is that of a first bevel angle A (see FIG.

5) which is in the range of about 90 to about 130 degrees, with 110 degrees constituting the preferred embodiment thereof. Another defining aspect of the invention is that of angle B which is a second bevel angle of lower bevel surface 20 relative to a transverse radial cross-section (axial radius) of the implant 14. This angle is in a range of about 20 to about 30 degrees.

It is also noted that the ratio of thread pitch, that is, the distance between successive pitch surfaces 16 and thread depth (as defined by minor thread diameter 22) is in the range of 1.25:1 to 1.40:1. This relationship differs materially from prior art ratios (see FIG. 1) in which the ratio of thread pitch to thread depth is approximately 1 to 1.

It has been found that the above combination of pitches per axial length, ratio of lengths of upper-to-lower bevel surfaces, and said total included bevel angle A, produce a resultant dental implant having far superior anatomical compatibility and durability than prior art dental implants. There is, as such, obtained an implant having substantial resistance to micro-mechanical axial, rotational and other movements resultant from forces, stresses and strains which are typically encountered, over time, by the implant.

It is noted that the axial face of each bevel surface 16 (the major thread diameter) is in a preferred embodiment, flattened and will have a flat axial surface of about 0.001 inch.

In FIG. 6 is shown an embodiment of the invention including a rigid body 140 having a high aspect ratio, e.g., 4:1 of upper base 124 to lower base 126, and having a recessed head 122. As such, the upper base is much larger than the lower base.

In FIG. 7 is shown another embodiment in which a rigid body 240 includes a cylindrical upper portion 28 and a lower integral cylindrical section 30 having a taper of about nine degrees relative to cylindrical envelope 33 and a length of about 6 mm relative to a 12 mm length of the upper portion 28.

In FIG. 8 is shown a further embodiment in which a rigid body 340 includes cylindrical sections 34, 36 and 38 of successively smaller diameter. Such body 340 may have lengths of 8, 10 or 13 mm, and the sections thereof may have axial lengths of 2 to 5 mm.

It is also noted that a dental implant in accordance with the present invention may be provided with any type of head. Also, the implant may be self-tapping.

It is yet further noted that an implant of the instant type may be advantageously used as a bone screw in orthopedic applications.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the claims appended herewith.

What is claimed is:

1. A bone implant comprising:
   a rigid body having thereupon axially symmetric and radially circumferential spiral pitch surfaces, in a range of about 22 to about 28 pitch surfaces per axial inch, an upper concave bevel surface above each pitch surface, which is longer than a lower bevel surface beneath each pitch surface, and an intersection of each plane of each pitch surface and each plane of each lower bevel surface defining a total included angle in a range of about 90 to about 130 degrees, said rigid body having minor thread diameters at intersections, between pitch surfaces, of said upper and lower bevel surfaces, said pitch surfaces and said minor thread diameters defining, at any axial radius of said rigid body, a ratio of thread pitch to thread depth in a range of about 1.25:1 to about 1.40:1.

2. The implant as recited in claim 1 in which each of said lower bevel surfaces define a total included angle in a range of about 20 to about 30 degrees relative to any given axial radius cross-section of said implant at a minor thread diameter thereof.

3. The implant as recited in claim 2, in which said lower bevel surfaces comprise substantially flat surfaces.

4. The implant as recited in claim 2, in which said concave upper bevel surfaces of said pitch surfaces each define a radius in a range of about 0.040 inches.

5. The implant as recited in claim 2, in which said pitch surface comprise, at any axial radius, of said rigid body, a ratio of major thread diameter to said minor thread diameter in a range of about 1.2:1 to about 1.3:1.

6. The implant as recited in claim 5, in which the difference between said major and minor thread diameters, at an given axial radius comprises about 0.030 inches.

7. The Implant as recited in claim 2, in which a ratio of thread pitch to thread depth is, at any axial radius, in a range of about 1.25:1 to about 1.40:1.

8. The implant as recited in claim 2, in which said total included angle comprises about 110 degrees.

9. The implant as recited in claim 2, in which a length of said upper bevel surface comprises about twice the length of said lower bevel, at any axial radius of said rigid body.

10. The implant as recited in claim 2, comprising a buttress-thread dental implant.

11. The implant as recited in claim 2, comprising as orthopedic screw.

12. The implant as recited in claim 2, in which said rigid body, thereof defines an envelope in the form of a conical section.

13. The implant as recited in claim 12, in which a ratio of diameters of a major base to a lower base of said conical section is characterized by a ratio in a range of 1.5:1 to 4:1.

14. The implant as recited in claim 2, in which said rigid body thereof defines an envelope having an upper portion substantially defining a cylinder and an integral lower portion substantially defining a conical section.

15. The implant as recited in claim 2, in which an envelope defined by said rigid body substantially defines cylindrical sections of greater diameter at an upper region of said rigid body and of smaller diameter at lower regions of said body.

16. The implant as recited in claim 15, in which said rigid body comprises three cylindrical regions each of successively lesser diameter from top to bottom thereof.

* * * * *